(12) United States Patent
Hsieh et al.

(10) Patent No.: US 8,048,426 B2
(45) Date of Patent: Nov. 1, 2011

(54) **EXTRACTS FROM *CHLORELLA***

(75) Inventors: Hsing-Pang Hsieh, Miaoli County (TW); Tsu-An Hsu, Taipei (TW); Yu-Sheng Chao, Warren, NJ (US); Yu-Cheng Chou, Miaoli County (TW); Shun Te Wang, Taichung (TW)

(73) Assignee: International Chlorella Co., Ltd., Taichung (TW)

( * ) Notice: Subject to any disclaimer, the term of this patent is extended or adjusted under 35 U.S.C. 154(b) by 206 days.

(21) Appl. No.: 12/252,662

(22) Filed: Oct. 16, 2008

(65) Prior Publication Data

US 2009/0111876 A1    Apr. 30, 2009

Related U.S. Application Data

(60) Provisional application No. 60/982,535, filed on Oct. 25, 2007.

(51) Int. Cl.
*A61K 31/20*    (2006.01)
*A61K 36/05*    (2006.01)
*A61K 36/02*    (2006.01)

(52) U.S. Cl. .................................. 424/195.17; 514/558

(58) Field of Classification Search .......................... None
See application file for complete search history.

(56) References Cited

U.S. PATENT DOCUMENTS

| | | | |
|---|---|---|---|
| 5,879,941 | A | 3/1999 | Schmidt et al. |
| 5,985,634 | A | 11/1999 | Schmidt et al. |
| 5,998,700 | A | 12/1999 | Lightfoot et al. |
| 6,329,573 | B1 | 12/2001 | Lightfoot et al. |
| 6,689,589 | B2 | 2/2004 | Huisman et al. |
| 6,749,884 | B1* | 6/2004 | Morimatsu et al. |
| 6,815,580 | B1 | 11/2004 | Miller et al. |
| 7,081,357 | B2 | 7/2006 | Huisman et al. |
| 7,172,691 | B2 | 2/2007 | Dunlop et al. |
| 7,172,782 | B2 | 2/2007 | Howarth |
| 7,182,966 | B2 | 2/2007 | Howarth |
| 7,195,782 | B2 | 3/2007 | Moore et al. |
| 7,229,804 | B2 | 6/2007 | Huisman et al. |
| 2001/0000266 | A1 | 4/2001 | Schmidt et al. |
| 2002/0062495 | A1 | 5/2002 | Schmidt et al. |
| 2004/0128710 | A1 | 7/2004 | Schmidt et al. |
| 2007/0197626 | A1* | 8/2007 | Dittrich-Wengenroth et al. |

FOREIGN PATENT DOCUMENTS

| | | |
|---|---|---|
| EP | 0859849 A1 | 8/1998 |
| EP | 0859849 B1 | 7/2006 |
| EP | 1808483 | 7/2007 |
| JP | 10248553 A2 | 9/1998 |
| WO | 97/12983 | 4/1997 |

OTHER PUBLICATIONS

Patterson, GW. Lipids, 1969; 5(7): 597-600. Effect of culture temperature on fatty acd compositon of *Chlorella sorokiniana* [citaton omitted].*

Yoshida et al. "Purification and Characterization of Cadmium-Binding Protein from Unicelluar Alga *Chlorella sorokinian*" Current Microbiology, vol. 52(2006), pp. 460-463.
Rodriguez-Lopez et al. "Plasma-Glucose and Plasma-Insulin in Normal and Alloxanized Rats Treated with *Chlorella*" Life Sciences, vol. 10, Part II, pp. 57-60, 1971, Great Britain.
Lee et al. "Hypoglycemic Action of *Chlorella*", Department of Biochemistry, Taipei Medical College, Received for Publication, Feb. 8, 1977, pp. 102-106, with English Abstract (p. 106).
Sun et al. "Extraction, initial purification and inhibitory activity of growth-inhibitor formed by *Isochrysis galbana*", Huadong Ligong Daxue Xuebao /Journal of East China University of Science and Technology, vol. 33, Issue 3, Jun. 2007, pp. 340-344+368, Abstract.
Li et al. "Isolation and purification of canthaxanthin from the microalga *Chlorella zofingiensis* by high-speed counter-current chromatography", Journal of Separation Science, vol. 29, Issue 5, Mar. 2006, pp. 699-703, Abstract.
Park et al. "*Chlorella* dichloromethane extract ameliorates NO production and iNOS expression through the down-regulation of NfkB activity mediated by suppressed oxidative stress in RAW 264.7 macrophages", Clinica Chimica Acta, vol. 351, Issue 1-2, Jan. 2005, pp. 185-196, Abstract.
Oshima et al., "Development of a solid-phase extraction method for determination of pheophorbide a and pyropheophorbide a in health foods by liquid chromatography", Journal of AOAC International, vol. 87, Issue 4, Jul. 2004, pp. 937-942, Abstract.
Mendes et al. "Supercritical carbon dioxide extraction of compounds with pharmaceutical importance from microalgae", Inorganica Chimica Acta, vol. 356, Dec. 3, 2003, pp. 328-334, Abstract.
Li et al. "Preparative isolation and purification of lutein from the microalga *Chlorella vulgaris* by high-speed counter-current chromatography", Journal of Chromatography A vol. 905, Issue 1-2, Jan. 5, 2001, pp. 151-155, Abstract.
Miranda et al. "Antioxidant activity of the microalga *Chlorella vulgaris* cultered on special conditions", Bollettino Chimico Farmaceutico, vol. 140, Issue 3, 2001, pp. 165-168, Abstract.
Maeda et al. "Bioaccumulation of Antimony by *Chlorella vulgaris* and the Association Mode of Antimony in the Cell", Applied Organometallic Chemistry, vol. 11, Issue 5, May 1997, pp. 393-396, Abstract.
Dhillon et al. "Biocidal activity of algal toxins against immature mosquitoes", Journal of Chemical Ecology, vol. 8, Issue 2, Feb. 1982, pp. 557-566, Abstract.
Rigano et al. "Temperature dependence of nitrate reductase in the psychrophilic unicellular alga *Koliella antarctica* and the mesophilic alga *Chlorella sorokiniana*", Plant, Cell and Environment, vol. 29, Issue 7, Jul. 2006, pp. 1400-1409, Abstract.
Vona et al. "Temperature responses of growth, photosynthesis, respiration and NADH: Nitrate reductase in cryophilic and mesophilic algae", New Phytologist, vol. 163, Issue 2, Aug. 2004, pp. 325-331, Abstract.

(Continued)

*Primary Examiner* — Michele Flood
(74) *Attorney, Agent, or Firm* — Occhiuti Rohlicek & Tsao LLP

(57) ABSTRACT

An invention relates to an extract of *Chlorella sorokiniana*, which contains myristic acid, palmitic acid, palmitoleic acid, oleic acid, linoleic acid, linolenic acid, and stearic acid. Also related is use of this extract to treat diabetes, obesity, and dyslipidaemia.

17 Claims, No Drawings

OTHER PUBLICATIONS

Matsukawa et al. "Antioxidants from carbon dioxide fixing *Chlorella sorokiniana*", Journal of Applied Phycology, vol. 12, Issue 3-5, 2000, pp. 263-267, Abstract.

Maskey et al. "Quinazolin-4-one derivatives from *Streptomyces* isolates", J Nat Prod. Jul. 2004:67(7):1131-4, Abstract.

* cited by examiner

EXTRACTS FROM *CHLORELLA*

CROSS-REFERENCE TO RELATED APPLICATIONS

This application claims priority from U.S. Provisional Patent Application No. 60/982,535, filed Oct. 25, 2007. The content of the prior application is incorporated herein by reference in its entireties.

BACKGROUND

Peroxisome proliferator-activated receptors (PPARs) belong to a family of nuclear receptors that control many cellular and metabolic processes. Three mammalian PPARs have been identified, i.e., PPARα, PPARδ, and PPARγ. See Lee C. H. et al., *Endocrinology* 2003, 144: 2201-7. Upon activation, PPARs trigger a cascade of transcriptional events leading to altered lipid and glucose metabolism. See, e.g., Willson T. M. et al., *J Med Chem* 2000, 43, 527-50; and Moraes L. A. et al., *Pharmacol Ther.* 2006, 110, 371-85.

Given their roles in lipid and glucose metabolism, PPARs are promising therapeutic targets of diseases, such as type II diabetes, obesity, hepatitis C, dyslipidemia, coronary heart disease, inflammatory disease, and cancer. For example, glitazones, PPARγ agonists, have been used to treat type II diabetes. As another example, fibrates, PPARα agonists, are effective medications that lower blood triglyceride levels. However, most PPAR therapeutics have limited efficacy or significant side effects.

There is still a need to develop more effective drugs for controlling lipid and glucose metabolism via modulation of PPAR activity.

SUMMARY

This invention is based on a discovery that an extract of *Chlorella sorokiniana*, a single-cell thermophilic green alga, effectively activates PPARα and PPARγ. Thus, in one aspect, this invention relates to an extract containing myristic acid, palmitic acid, palmitoleic acid, oleic acid, linoleic acid, linolenic acid, and stearic acid, which, respectively, constitute 0.1% to 5%, 10% to 60%, 2% to 15%, 2% to 15%, 2% to 15%, 0.8% to 6%, and 0.5% to 5% of the dry weight of the extract. Preferably, the myristic acid, the palmitic acid, the palmitoleic acid, the oleic acid, the linoleic acid, the linolenic acid, and the stearic acid constitute 0.5% to 4%, 15% to 50%, 3.5% to 12%, 3.5% to 12%, 3% to 12%, 1.2% to 5%, and 0.8% to 4% of the dry weight of the extract, respectively. More preferably, the extract contains the seven components, in the above order, at 0.7% to 1.7%, 19.2% to 43.6%, 4.4% to 10.1%, 4.4% to 10.0%, 3.9% to 8.8%, 1.8% to 4.0%, and 1.1% to 2.6% of the dry weight of the extract, respectively.

The extract may further contain hexadecadienoic acid, hexadecenoic acid, and octadecenoic acid, which constitute 0.8% to 6%, 1.2% to 8%, and 1.2% to 8% of the dry weight of the extract, respectively. In one embodiment, the hexadecadienoic acid, the hexadecenoic acid, and the octadecenoic acid constitute 1.2% to 5%, 2% to 7%, and 2% to 7% of the dry weight of the extract, respectively. For example, the extract also contains hexadecadienoic acid, hexadecenoic acid, and octadecenoic acid at 1.9% to 4.3%, 2.6% to 6.0%, and 2.6% to 5.9% of the dry weight of the extract, respectively.

In another aspect, this invention relates to a method of treating diabetes, obesity, or dyslipidaemia. The method includes administering to a subject in need an effective amount of the above-described extract.

Also within the scope of this invention are a pharmaceutical composition containing the above-described extract and a pharmaceutically acceptable carrier, use of such a composition to treat diabetes, obesity, or dyslipidaemia, and use of such a composition for the manufacture of a medicament for treating these disorders.

Details of several embodiments of the invention are set forth in the description below. Other features, objects, and advantages of the invention will be apparent from the description, and also from the claims.

DETAILED DESCRIPTION

The extract of this invention can be prepared by extraction of *Chlorella sorokiniana* with ethyl acetate. The extract thus obtained can be further purified by thin layer chromatography, flash column chromatography, high performance liquid chromatography, or any other suitable methods. An actual example is provided below.

The extract effectively activates PPARα/γ, resulting in altered lipid and glucose metabolism. It can therefore be used to treat diabetes, obesity, or dyslipidaemia. Thus, this invention relates to a method of treating one of the disorders by administering to a subject in need thereof an effective amount of the extract. The term "an effective amount" refers to an amount of the extract which is required to confer the above-described therapeutic effect in the subject. Effective amounts may vary, as recognized by those skilled in the art, depending on route of administration, excipient usage, and the possibility of co-usage with other agents. The term "treating" refers to administering the extract to a subject that has diabetes, obesity, or dyslipidaemia, or has a predisposition toward one of the disorders, with the purpose to cure, heal, alleviate, relieve, alter, remedy, ameliorate, improve, or affect the target disorder, the symptoms of the target disorder, or the predisposition toward the target disorder.

To practice one of the above-described methods, one administers to a subject in need thereof orally, rectally, parenterally, by inhalation spray, or via an implanted reservoir a composition that is either the above-mentioned extract alone or a mixture of the extract and a pharmaceutically acceptable carrier. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides).

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762. Creams are preferably formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% almond and about 70% white soft paraffin by weight.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with one or more of active compounds of the extract), can be utilized as pharmaceutical excipients for delivery of the active compounds. Examples of other carriers include colloidal silicon dioxide, magnesium stearate, cellulose, sodium lauryl sulfate, and D&C Yellow #10.

A suitable in vitro assay can be used to preliminarily evaluate the efficacy of an extract of this invention in activating PPARα/γ. See the example described below. The extract can further be examined for its efficacy in treating diabetes, obesity, or dyslipidaemia. For example, the extract can be administered to an animal (e.g., a mouse model) having a disorder and its therapeutic effects are then accessed. Based on the results, an appropriate dosage range and administration route can also be determined.

Without further elaboration, it is believed that the above description has adequately enabled the present invention. The following specific examples are, therefore, to be construed as merely illustrative, and not limitative of the remainder of the disclosure in any way whatsoever. All of the publications, including patents, cited herein are hereby incorporated by reference in their entirety.

EXAMPLE 1

Preparation of *Chlorella Sorokiniana* Extracts

A crude *Chlorella sorokiniana* water solution (W87-10) was provided by International Chlorella Co. Ltd., Chang-Hua County, Taiwan, R.O.C. It was prepared as follows:

Cryptomonadales was seeded in a culture bottle containing nutrition medium. Air was continuously bubbled into the nutrition medium, while the bottle was agitated on a shaker. Cryptomonadales was cultured about 1.5 months.

The cryptomonadales algae was harvested by the ALFA-LAVEL centrifuge and dried by a spray dryer to form a powder. 70 kg of water was added to 30 kg of the cryptomonadales powder. The mixture was boiled at 100° C. for 30 minutes. The undissolved residue was removed by centrifugation and the supernatant was collected. Approximately 95% of water was removed from the supernatant using a vacuum dryer. The remaining suspension was filtered and decolored to afford a crude *Chlorella sorokiniana* solution.

100 ml of the crude solution was diluted with water twice the original volume and was then subjected to extraction with EtOAc (200 mL×4). The organic layer was then concentrated under reduced pressure. The residue was charged onto a silica gel column and eluted with gradient acetone-n-hexane (30%-100%) to afford 8 fractions (CE1: 7.0 mg, CE2: 17.9 mg, CE3: 59.0 mg, CE4: 60.9 mg, CE5: 68.4 mg, CE6: 115.7 mg, CE7: 33.4 mg, and CE8: 170.2 mg).

Fraction CE3 was further purified using preparative TLC and developed with 33% EtOAc in n-hexane to obtain six sub-fractions (CE3-1: 5.3 mg, CE3-2: 1.3 mg, CE3-3: 25.6 mg; CE3-4: 3.5 mg, CE3-5: 15.5 mg, and CE3-6: 5.6 mg).

8.2 mg of CE3-3 was dissolved in dichloromethane (0.6 mL) and mixed with 20% boron trifluride etherate in methanol (4 mL) under nitrogen gas. The solution was then sealed and stirred at 100° C. for 5.0 min. After cooling, the solution was neutralized by addition of saturated sodium chloride aqueous solution (10 mL) and then subjected to extraction with n-hexane (2 mL). The organic layer was dried with $MgSO_4$ and concentrated under reduced pressure to give a methyl ester product as yellow colored oil (CE3-3M). The composition of CE3-3M was analyzed using a Hewlett-Packard 6890 gas chromatography system coupled with a HP 5973 mass selective detector, a HP 7673 automatic liquid sampler, and an Agilent DB-5MS column (30 cm×250 μm; film thickness, 0.25 μm). Helium was used as the carrier gas at a flow rate of 1 mL/min. The inlet temperature was maintained at 250° C. The sample (1 μL) was injected with a 1:50 split ratio. The initial oven temperature was maintained at 120° C. for 3 min and programmed to increase to 180° C. at a rate of 10° C./min (held for 1 min) then to 210° C. at a rate of 2° C./min (held for 5 min), with a total run time of 30 min. Mass spectra were recorded over a 50-550 amu range, with 70 eV ionization energy and 230° C. MS source temperature. Data collection and integration were performed by the HP Chem Station software. The quantity of each component were determined by integrating the peak area of the total ions current spectrograms and transformed into percentage. The components were identified by comparison of their retention times with commercial standard compounds and the National Institute of Standards And Technology MS Search program.

Ten fatty acids were observed from GC chromatogram and seven of them were confirmed by the GC-MS library search. The relative percentages and retention times of all these fatty acids are shown in the table below:

| no. | Compound name | | Retention Time (min.) | Relative % |
|---|---|---|---|---|
| 1 | myristic acid [tetradecanoic acid] | C14:0 | 11.9 | 1.7 |
| 2 | hexadecadienoic acid | C16:2 | 15.6 | 4.3 |

-continued

| no. | Compound name | | Retention Time (min.) | Relative % |
|---|---|---|---|---|
| 3 | hexadecenoic acid | C16:1 | 15.9 | 6.0 |
| 4 | palmitoleic acid [(Z)-9-hexadecenoic acid] | C16:1 | 15.9 | 10.1 |
| 5 | palmitic acid [hexadecanoic acid] | C16:0 | 16.6 | 43.6 |
| 6 | linoleic acid [(Z),(Z)-9-12--octadecadienoic acid] | C18:2 | 21.5 | 8.8 |
| 7 | linolenic acid [(Z),(Z),(Z)-9-,12-,15--octadecadienoic acid] | C18:3 | 21.7 | 4.0 |
| 8 | oleic acid [(Z)-9-octadecenoic acid] | C18:1 | 21.8 | 10.0 |
| 9 | octadecenoic acid | C18:1 | 22.0 | 5.9 |
| 10 | stearic acid [octadecanoic acid] | C18:0 | 22.7 | 2.6 |

EXAMPLE 2

Bioassays

CE3 and CE3-3 were studied for their efficacy in activating PPARα/γ in the following assays.

PPARγ Ligand Binding Assay

The ligand binding domain of hPPARγ was expressed in *E. coli* as glutathione S-transferase (GST) fusion proteins. The recombinant proteins were isolated by affinity purification using glutathione-sepharose (Amersham Biosciences, NJ) following the manufacturer's instructions. The recombinant GST-hPPARγ$^{LBD}$ preparations were used at a final concentration of approximately 5 nM. Goat anti-GST antibodies (Catalog number 27-4577-01, Amersham Biosciences, NJ) were used at a dilution of 1:2000. Protein A-yttrium silicate scintillation proximity assay beads (catalog number RPN143, Amersham Biosciences, NJ) were suspended in 50 mL of an assay buffer containing 10 mM Tris-Cl, pH 7.2, 1 mM EDTA, 10% (w/v) glycerol, 10 mM sodium molybdate, 1 mM dithiothreitol, 0.5 mM phenylmethylsulfonyl fluoride, 2 μg/mL benzamidine, and 0.01% sodium azide.

A sample extract was dissolved in DMSO to obtain a final concentration of 5 μg/mL. The radiolabeled PPAR ligand [$^3$H] rosiglitazone (60 Ci/mmol) (American Radiolabeled Chemicals, MO) was diluted 425-fold in ethanol and used at a final concentration of 7.8 nM.

To a 96-well microtiter plate (Catalog number 6005290, Packard Instrument, CT) were sequentially added the GST-PPARγ$^{LBD}$, the goat anti-GST antibodies, the well-suspended protein A-yttrium silicate scintillation proximity assay beads, the sample extract, and the diluted [$^3$H] rosiglitazone solution (20 μL each). The plate was incubated with gentle shaking at 4° C. After 24 hours, the level of radioactivity was quantified using a Topcount® Microplate Scintillation & Luminescence Counter (Packard Instrument Co., Inc, USA).

The results showed that both CE3 and CE3-3 had potent binding activity: while CE3 exhibited >95% displacement of [$^3$H] rosiglitazone bound to PPARγ$^{LBD}$, CE3-3 exhibited 99.8% displacement of [$^3$H] rosiglitazone. IC$_{50}$ values for PPARγ$^{LBD}$ were determined using dose response curves with 8 data points in triplicates. The IC$_{50}$ values of CE3 and CE3-3 were 2.7 μg/mL and 1.6 μg/mL, respectively.

PPARα Charcoal Binding Assay

The charcoal binding assay was conducted in manners similar to those described in Mahindroo, et al., *J Med Chem* 2005, 48: 8194-208; Mahindroo N. et al., *J Med Chem* 2006, 49: 1212-6; Mahindroo N. et al., *J Med Chem* 2006, 49: 6421-6424; Lu, I. L. et al., *J Med Chem* 2006, 49: 2703-12.

Assay solutions containing TEGM buffer (10 mM Tris, pH 7.2, 1 mM EDTA, 10% glycerol, 7 μL/100 mL of β-mercaptoethanol, 10 mM sodium molybdate, 1 mM dithiothreitol, 2 μg/mL benzamide, and 0.5 mM phenylmethylsulfonyl fluoride) and 2.5 nM [$^3$H] L-783,483 (79 μCi/mmol, synthesized by the Division of Biotechnology and Pharmaceutical Research, National Health Research Institutes, Taiwan), with or without a sample extract, were prepared. The assay solutions were incubated at 4° C. for 24 hours in a final volume of 300 μL. The unbound ligand was removed by incubating on ice with 200 μL of dextran/gelatin-coated charcoal for 10 min. After centrifugation at 4° C. at 3,000 rpm for 10 min, radioactivity of the supernatant was counted in a TRI-CARB 2100TR® liquid scintillation analyzer.

IC$_{50}$ values for displacing the binding of [$^3$H] L-783,483 to PPARα$^{LBD}$ were determined using dose response curves with 6 data points in triplicates. The IC$_{50}$ values for CE3 and CE3-3 were 5.0 and 2.3 μg/mL, respectively.

PPAR Transcriptional Activation Assay

Human hepatoma Huh7 cell lines were seeded (5×10$^4$ cells/well) in 24-well cell culture plates in high glucose Dulbecco's modified Eagle's medium (DMEM) containing 10% fetal bovine serum, 100 units/mL penicillin G, 100 mg/mL streptomycin sulfate, and 0.25 μg/mL amphotericin B at 37° C. under a humidified 5% CO$_2$ atmosphere. After 24 hours, transfection was performed using the Fugene 6® transfection reagent (Roche, Germany) according to the manufacturer's instructions. Specifically, a transfection mixture was prepared by adding 0.5 μl of Fugene 6, 0.05 μg of pGAL4-PPARγ$^{LBD}$ plasmid, 0.14 μg of pG5-TK-Luc reporter, and 0.25 ng of a pRL-SV40 Renilla luciferase plasmid as the transfection internal control to each well. Huh7 cells were incubated in the transfection mixture at 37° C. overnight under 5% CO$_2$. The cells were then incubated for 24 h in fresh high-glucose DMEM in the presence of sample extract DMSO solutions at various concentrations. Control cells were incubated in DMSO.

After 24 hours, the cells were harvested and the cell lysates were produced using Passive® Lysis Buffer (Promega, Wis.) following the manufacturer's instructions. Luciferase activity in cell extracts was determined using a Dual-Luciferase® Reporter Assay kit (Promega, Madison, Wis.) and counted in a SIRIUS-0 luminometer (Berthold detection systems, Pforzheim, Germany). Briefly, 50 μL of Luciferase Assay Reagent II (LARII) was added into a vial containing 5 μL of cell lysate and then the Firefly Luciferase activity of the mixture was measured. 50 μL of Stop & Glo® Reagent was added to the vial and the Renilla Luciferase activity of the mixture was measured. The highest DMSO concentration used in the assay was 0.1%, which was found to have no effect on transactivation activity. In all theses results, activation by PPAR ligand rosiglitazone (2 μM) was used as a positive control. The transactivation results were expressed as the ratio of Firefly Luciferase signal over the Renilla Luciferase signal.

CE3 achieved 55.6% of the maximum PPARγ activation of the positive control and CE3-3 achieved 63.4% of the maximum PPARγ activation of the positive control.

Preadipocyte Differentiation Assay

Confluent preadipocyte 3T3-L1 cells were incubated in DMEM containing 10% fetal calf serum, 100 units/mL penicillin G, 10 μg/mL streptomycin sulfate, and 150 nM insulin, in the absence or presence of test fractions at 37° C. in 5% CO$_2$ for 3 days. The cells were kept under these conditions until the appearance of adipocytes (about nine days) with the medium changed every two days. Cells which differentiated into adipocytes were stained with Oil Red-O (Sigma) as described in Trouba K. J. et al.,. *Toxicol Appl Pharmacol* 2000, 168, 25-35. Briefly, cells were fixed in 10% formalin for at least 1 h and stained by immersion in Oil Red-O for 2 h then exhaustively rinsed with water. Samples were then dried by incubation at 32° C.

CE 3 and CE 3-3 showed moderate adipogenic differentiation activity of 3T3-L1 preadipocytes.

OTHER EMBODIMENTS

A number of embodiments of the invention have been described. Nevertheless, it will be understood that various modifications may be made without departing from the spirit and scope of the invention. Accordingly, other embodiments are also within the scope of the following claims.

The details of one or more embodiments of the invention are set forth in the accompanying drawings and the description below. Other features, objects, and advantages of the invention will be apparent from the description and drawings, and from the claims.

What is claimed is:

1. An extract of *Chlorella sorokiniana*, comprising myristic acid, palmitic acid, palmitoleic acid, oleic acid, linoleic acid, linolenic acid, and stearic acid; wherein the myristic acid, the palmitic acid, the palmitoleic acid, the oleic acid, the linoleic acid, the linolenic acid, and the stearic acid constitute 0.1% to 5%, 10% to 60%, 2% to 15%, 2% to 15%, 2% to 15%, 0.8% to 6%, and 0.5% to 5% of the total dry weight of the extract, respectively.

2. The extract of claim 1, wherein the myristic acid, the palmitic acid, the palmitoleic acid, the oleic acid, the linoleic acid, the linolenic acid, and the stearic acid constitute 0.5% to 4%, 15% to 50%, 3.5% to 12%, 3.5% to 12%, 3% to 12%, 1.2% to 5%, and 0.8% to 4% of the total dry weight of the extract, respectively.

3. The extract of claim 2, wherein the myristic acid, the palmitic acid, the palmitoleic acid, the oleic acid, the linoleic acid, the linolenic acid, and the stearic acid constitute 0.7% to 1.7%, 19.2% to 43.6%, 4.4% to 10.1%, 4.4% to 10.0%, 3.9% to 8.8%, 1.8% to 4.0%, and 1.1% to 2.6% of the total dry weight of the extract, respectively.

4. The extract of claim 1, further comprising hexadecadienoic acid; wherein the hexadecadienoic acid constitutes 0.8% to 6% of the total dry weight of the extract.

5. The extract of claim 4, wherein the hexadecadienoic acid, constitutes 1.2% to 5%, of the total dry weight of the extract.

6. The extract of claim 5, wherein the hexadecadienoic acid constitutes 1.9% to 4.3%, of the total dry weight of the extract.

7. The extract of claim 2, further comprising hexadecadienoic acid; wherein the hexadecadienoic acid constitutes 0.8% to 6%, of the total dry weight of the extract.

8. The extract of claim 7, wherein the hexadecadienoic acid constitutes 1.2% to 5%, of the total dry weight of the extract.

9. The extract of claim 8, wherein the hexadecadienoic acid constitutes 1.9% to 4.3%, of the total dry weight of the extract.

10. The extract of claim 3, further comprising hexadecadienoic acid wherein the hexadecadienoic acid constitutes 0.8% to 6%, of the total dry weight of the extract.

11. The extract of claim 10, wherein the hexadecadienoic acid constitutes 1.2% to 5%, of the total dry weight of the extract.

12. The extract of claim 11, wherein the hexadecadienoic acid constitutes 1.9% to 4.3% of the total dry weight of the extract.

13. A pharmaceutical composition comprising the extract of claim 1 and a pharmaceutically acceptable carrier.

14. The pharmaceutical composition of claim 13, wherein the myristic acid, palmitic acid, palmitoleic acid, oleic acid, linoleic acid, linolenic acid, and stearic acid constitute 0.5% to 4%, 15% to 50%, 3.5% to 12%, 3.5% to 12%, 3% to 12%, 1.2% to 5%, and 0.8% to 4% of the total dry weight of the extract, respectively.

15. The pharmaceutical composition of claim 14, wherein the myristic acid, the palmitic acid, the palmitoleic acid, the oleic acid, the linoleic acid, the linolenic acid, and the stearic acid constitute 0.7% to 1.7%, 19.2% to 43.6%, 4.4% to 10.1%, 4.4% to 10.0%, 3.9% to 8.8%, 1.8% to 4.0%, and 1.1% to 2.6% of the total dry weight of the extract, respectively.

16. The pharmaceutical composition of claim 13, wherein the extract further comprises hexadecadienoic acid; and, wherein the hexadecadienoic acid constitutes 0.8% to 6% of the total dry weight of the extract.

17. The pharmaceutical composition of claim 16, wherein the hexadecadienoic acid constitutes 1.2% to 5%, of the total dry weight of the extract.

* * * * *